(12) United States Patent
Yi et al.

(10) Patent No.: US 11,174,234 B2
(45) Date of Patent: Nov. 16, 2021

(54) CRYSTAL FORM OF 4-PHENYLTHIAZOLE DERIVATIVE AND PREPARATION METHOD THEREOF

(71) Applicant: SICHUAN KELUN PHARMACEUTICAL RESEARCH INSTITUTE CO., LTD., Sichuan (CN)

(72) Inventors: Shidong Yi, Sichuan (CN); Zheng Gong, Sichuan (CN); Tianming Wang, Sichuan (CN); Chengxi Yang, Sichuan (CN); Lichun Wang, Sichuan (CN); Jingyi Wang, Sichuan (CN)

(73) Assignee: Sichuan Kelan Pharmaceutical Research Institute Co., Ltd., Sichuan (CN)

( * ) Notice: Subject to any disclaimer, the term of this patent is extended or adjusted under 35 U.S.C. 154(b) by 0 days.

(21) Appl. No.: 17/053,893

(22) PCT Filed: May 29, 2019

(86) PCT No.: PCT/CN2019/088959
§ 371 (c)(1),
(2) Date: Nov. 9, 2020

(87) PCT Pub. No.: WO2019/233328
PCT Pub. Date: Dec. 12, 2019

(65) Prior Publication Data
US 2021/0269410 A1    Sep. 2, 2021

(30) Foreign Application Priority Data

Jun. 8, 2018 (CN) .......................... 201810585583.7

(51) Int. Cl.
C07D 277/46    (2006.01)
(52) U.S. Cl.
CPC ........ C07D 277/46 (2013.01); *C07B 2200/13* (2013.01)
(58) Field of Classification Search
CPC .......................... C07D 277/46; C07B 2200/13
See application file for complete search history.

(56) References Cited

U.S. PATENT DOCUMENTS

2015/0148385 A1    5/2015 Kano et al.

FOREIGN PATENT DOCUMENTS

| CN | 1419547 A | 5/2003 |
| CN | 101809008 A | 8/2010 |
| CN | 103450110 A | 12/2013 |
| CN | 105992761 A | 10/2016 |
| CN | 106083759 A | 11/2016 |
| CN | 109970678 A | 7/2019 |
| WO | WO2015/093586 A1 * | 6/2015 |
| WO | 2018149309 A1 | 8/2018 |

OTHER PUBLICATIONS

International Search Report dated Sep. 6, 2019 in PCT/CN2019/088959.
Written Opinion dated Sep. 6, 2019 in PCT/CN2019/088959.
Dou, Ying, "Recrystalization," Inorganic and Analytical Chemistry Laboratory Fascicle of University Chemical Laboratory, Aug. 31, 2015, p. 49.
Guo, Yonghui et al., "Application of Differential Scanning Calorimetry in the Research of Crystalline Drugs," 2010.
D. Giron, "Thermal analysis and calorimetric methods in the characterisation of polymorphs and solvates," Thermochimica Acta 248 (1995) 1-59, Elsevier Science B.V. 1995.

* cited by examiner

*Primary Examiner* — Timothy R Rozof
(74) *Attorney, Agent, or Firm* — Ice Miller LLP

(57) ABSTRACT

The invention relates to a crystal form of 4-phenylthiazole derivative, a pharmaceutical composition comprising the same, a preparation method, and a use of the crystal form for the manufacture of a medicament for treating thrombocytopenia.

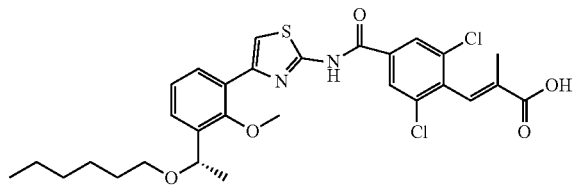

28 Claims, 4 Drawing Sheets

CRYSTAL FORM OF 4-PHENYLTHIAZOLE DERIVATIVE AND PREPARATION METHOD THEREOF

CROSS-REFERENCE TO RELATED APPLICATION

This application is a Section 371 of International Application No. PCT/CN2019/088959 filed May 29, 2019, which was published in the Chinese language Dec. 12, 2019, under International Publication No. WO 2019/233328 A1, which claims priority under 35 U.S.C. § 119(b) to Chinese Patent Application No. 201810585583.7 filed Jun. 8, 2018, the disclosures of which are incorporated herein by reference in their entireties.

TECHNICAL FIELD

The disclosure relates to crystal form of 4-phenylthiazole derivative and preparation method thereof.

BACKGROUND 4-phenylthiazole derivative (also known as Compound of formula I) having the following structure is useful for treating thrombocytopenia:

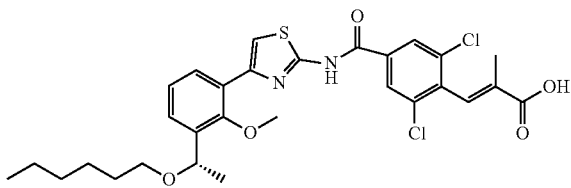

I

Thrombopoietin is polypeptide cytokines composed of 332 amino acids, which promotes thrombopoiesis via differentiation and proliferation of megakaryocytes stimulated by receptors. Therefore, the 4-phenylthiazole derivative can be used as a medicament for treating a condition of thrombocytopenia blood disease associated with abnormal platelet count.

Solid crystal form of a compound can essentially influence physical properties of the compounds, including but not limited to (1) filling performances like molar volume, density and hygroscopicity; (2) thermodynamic properties like melting temperature, vapour pressure and solubility; (3) kinetic properties like decomposition rate and stability (including stability under environmental conditions, especially under moisture and storage conditions); (4) surface properties like surface area, wettability, interfacial tension and appearance; (5) mechanical properties like hardness, tensile strength, compressibility, operability, fluidity and miscibility; or (6) filtering properties. Selection and control of solid crystal form are important for compounds of pharmaceutical formulations. Careful selection and control for solid crystal form may reduce issues with respect to synthesis, processing, formulation or administration relating to the compounds.

CN1419547A and US2015/0148385 A1 disclose the synthetic method of the compound. CN 101809008 A discloses a crystal form of the compound of formula I (designated as Crystal Form Y herein), which has main peaks at 2θ diffraction angles of 17.8, 21.1, 22.5, 23.3, 24.1, 24.4°.

SUMMARY OF THE INVENTION

The invention provides a Crystal Form D of the compound of formula I 4-phenylthiazole derivative (also designated as the Crystal Form according to the invention or Crystal Form D according to the invention or Crystal Form D).

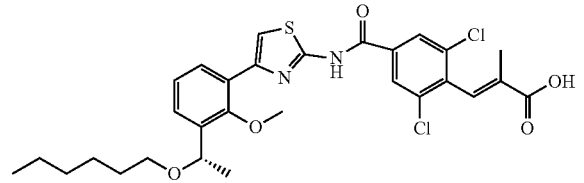

I

In an aspect, the invention provides a Crystal Form D of the compound of formula I, wherein the Crystal Form D has an X-ray powder diffraction (XRPD) pattern comprising peaks at diffraction angles (2θ) of about 4.9±0.2°, 6.0±0.2°, 12.5±0.2°, 18.3±0.2°, 18.9±0.2°, 21.0±0.2°, 23.8±0.2°.

In some preferable embodiments, the Crystal Form D has an X-ray powder diffraction (XRPD) pattern comprising peaks at diffraction angles (2θ) of about 4.9±0.2°, 6.0±0.2°, 7.3±0.2°, 12.5±0.2°, 18.3±0.2°, 18.9±0.2°, 19.7±0.2°, 21.0±0.2°, 22.2±0.2°, 23.8±0.2°.

In some preferable embodiments, the Crystal Form D has an XRPD pattern comprising peaks at diffraction angles (2θ) of about 4.9±0.2°, 6.0±0.2°, 12.5±0.2°, 14.7±0.2°, 15.6±0.2°, 17.1±0.2°, 18.3±0.2°, 18.9±0.2°, 21.0±0.2°, 23.8±0.2°, 24.9±0.2°.

In some preferable embodiments, the Crystal Form D has an XRPD pattern comprising peaks at diffraction angles (2θ) of about 4.9±0.2°, 6.0±0.2°, 7.3±0.2°, 12.5±0.2°, 14.7±0.2°, 15.6±0.2°, 17.1±0.2°, 18.3±0.2°, 18.9±0.2°, 19.7±0.2°, 21.0±0.2°, 22.2±0.2°, 23.8±0.2°, 24.9±0.2°.

In other preferable embodiments, the Crystal Form D has an XRPD pattern comprising peaks at diffraction angles (2θ) of about 4.1±0.2°, 4.9±0.2°, 6.0±0.2°, 6.2±0.2°, 8.7±0.2°, 9.8±0.2°, 10.1±0.2°, 12.5±0.2°, 13.4±0.2°, 14.0±0.2°, 14.7±0.2°, 15.6±0.2°, 17.1±0.2°, 17.9±0.2°, 18.3±0.2°, 18.5±0.2°, 18.9±0.2°, 19.9±0.2°, 21.0±0.2°, 21.3±0.2°, 21.8±0.2°, 22.7±0.2°, 23.4±0.2°, 23.8±0.2°, 24.9±0.2°.

In other preferable embodiments, the Crystal Form D has an XRPD pattern comprising peaks at diffraction angles (2θ) of about 4.1±0.2°, 4.9±0.2°, 6.0±0.2°, 6.2±0.2°, 7.3±0.2°, 8.7±0.2°, 9.8±0.2°, 10.1±0.2°, 12.5±0.2°, 13.4±0.2°, 14.0±0.2°, 14.7±0.2°, 15.6±0.2°, 17.1±0.2°, 17.9±0.2°, 18.3±0.2°, 18.5±0.2°, 18.9±0.2°, 19.7±0.2°, 19.9±0.2°, 21.0±0.2°, 21.3±0.2°, 21.8±0.2°, 22.2±0.2°, 22.7±0.2°, 23.4±0.2°, 23.8±0.2°, 24.9±0.2°.

In a more preferable embodiment, the Crystal Form D has an XRPD pattern comprising peaks at diffraction angles (2θ) which are substantially identical to those shown in FIG. 1.

In a further preferable embodiment, the Crystal Form D has an XRPD pattern with peaks which are substantially identical to those shown in FIG. 1.

In a more preferable embodiment, the Crystal Form D has an XRPD pattern as shown in FIG. 1.

In another aspect, the invention provides a process for preparing the Crystal Form D, comprising 1) dissolving the compound of formula I as solid in a good solvent for crystallization, 2) adding the solution obtained in step 1) to a poor solvent for crystallization for crystallization, 3) separating the resulting product and optionally subjecting it to drying to give the Crystal Form D, wherein the good solvent for crystallization is selected from an ether solvent, an ester solvent and a mixture thereof, and the poor solvent for crystallization is selected from an alkane solvent, an arene solvent and a mixture thereof.

In some embodiments, the volume ratio of the good solvent for crystallization to the poor solvent for crystallization is about 1:20-20:1, preferably about 1:1-1:10, more preferably 1:3-1:8, further preferably 1:4-1:7.

In some preferable embodiments, the good solvent for crystallization is an ether solvent or an ester solvent, preferably an ether solvent.

In some other preferable embodiments, the poor solvent for crystallization is an alkane solvent.

In some embodiments of the preparing process according the invention, the ester solvent is selected from ethyl acetate, propyl acetate, isopropyl acetate, butyl acetate, amyl acetate and a combination thereof, preferably selected from ethyl acetate, isopropyl acetate and a combination thereof.

In some other embodiments of the preparing process according the invention, the ether solvent is selected from diethyl ether, isopropyl ether, tetrahydrofuran, 1,4-dioxane and a combination thereof, preferably selected from tetrahydrofuran, 1,4-dioxane and a combination thereof.

In yet some other embodiments of the preparing process according the invention, the alkane solvent is selected from n-pentane, n-hexane, cyclohexane, n-heptane, octane and a combination thereof, preferably selected from n-pentane, n-hexane, n-heptane and a combination thereof, more preferably selected from n-pentane, n-hexane and a combination thereof.

In some other embodiments of the preparing process according the invention, the arene solvent is selected from benzene, toluene, xylene and a combination thereof.

In another aspect, the invention provides a pharmaceutical composition, comprising the Crystal Form D according to the invention and one or more pharmaceutically acceptable carriers.

In yet another aspect, the invention provides a use of the Crystal Form D according to the invention or the pharmaceutical composition according to the invention for the manufacture of a medicament for treating or preventing thrombocytopenia.

In yet another aspect, the invention provides the Crystal Form D according to the invention or the pharmaceutical composition according to the invention for use in treating or preventing thrombocytopenia.

In yet another aspect, the invention provides a method for treating or preventing thrombocytopenia, comprising administering a subject in need thereof the Crystal Form D according to the invention or the pharmaceutical composition according to the invention in an effective amount.

DETAILED DESCRIPTION

Figure 1:
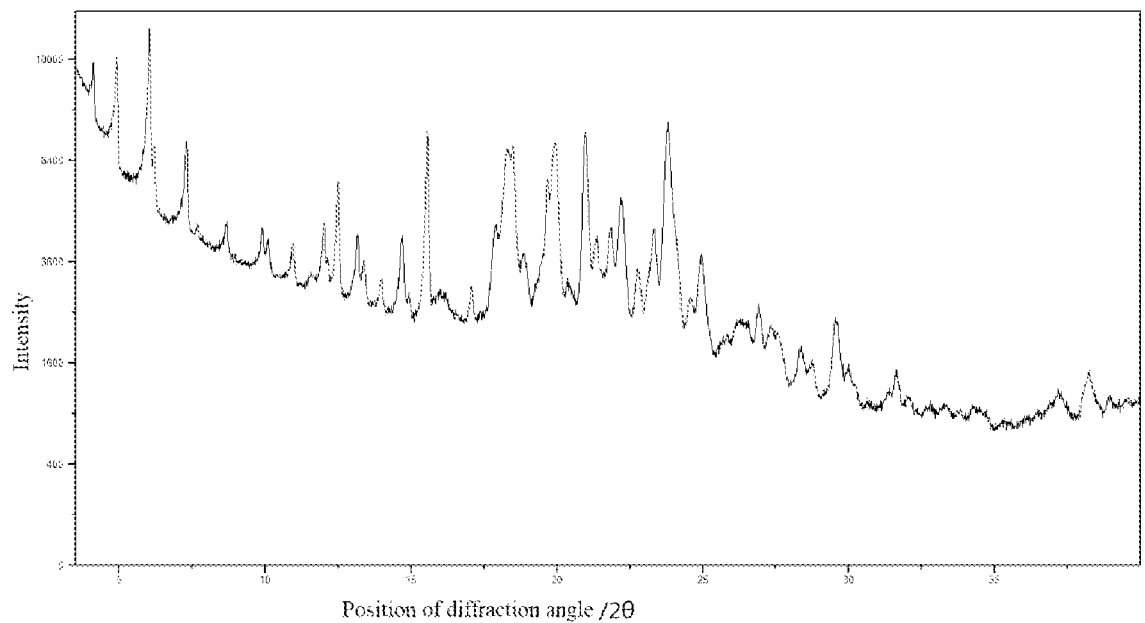
FIG. 1 shows the XRPD pattern of the Crystal Form D according to the invention (x-axis represents position of diffraction angle 2θ (°), y-axis represents intensity of diffraction).

The invention will be described in details and it will be understood that the description is for the purpose of illustration only rather than limitation thereto.

General Definition and Terminology

Unless stated otherwise, the technical and scientific terms used herein have the meanings identical to those understood by a person skilled in the art. The definitions provided herein will prevail in the case of contradiction. When a certain amount, concentration, or other value or parameter is set forth in the form of a range, a preferred range, or a preferred upper limit or a preferred lower limit, it should be understood that it is equivalent to specifically revealing any range formed by combining any upper limit or preferred value with any lower limit or preferred value, regardless of whether the said range is explicitly recited. Unless otherwise stated, the numerical ranges listed herein are intended to include the endpoints of the range and all integers and fractions (decimals) within the range.

When used with a numerical variable, the term "approximate" or "about" usually refers to the value of the variable and all the values of the variable within the experimental error (for example, within an average 95% confidence interval) or within ±10% of the specified value, or a wider range.

The expression "comprise" or its synonyms "contain", "include", "have" or the like is open-ended, which does not exclude other unlisted elements, steps or ingredients. The expression "consist of" excludes any unlisted elements, steps or ingredients. The expression "substantially consist of" refers to specified elements, steps or ingredients within a given range, together with optional elements, steps or components which do not substantively affect the basic and novel feature of the claimed subject matter. It should be understood that the expression "comprise" encompasses the expressions "substantially consist of" and "consist of".

The term "optional" or "optionally" means the event described subsequent thereto may or may not happen. This term encompasses the cases that the event may or may not happen.

As used herein, a value range (e.g. "1-10") and its subrange (e.g. "2-6", "6-10", "3-10" etc.) or the like encompass any within the value range (e.g. 1, 2, 3, 4, 5, 6, 7, 8, 9 or 10).

As used herein, the term "compound of formula I" refers to the compound 4-phenylthiazole derivative, which is represented by the following structure formula:

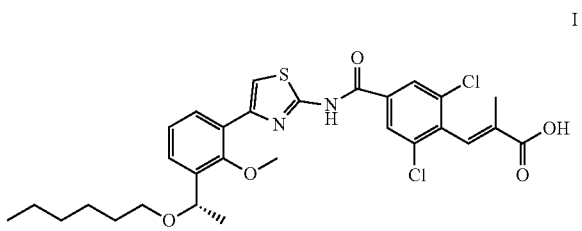 [SMILES: CCCCCCO[C@@H](C)c1cccc(-c2csc(NC(=O)c3cc(Cl)c(/C=C(\C)C(=O)O)c(Cl)c3)n2)c1OC]

As used in herein, the term "solid form" refers to that of the compound of formula I, for example, crystal form or amorphous form.

As used herein, the term "amorphous" refers to any solid substance which lacks order in three dimensions. In some cases, the amorphous solid can be characterized by known technology, including XRPD crystallography, differential scanning calorimetry (DSC), solid state nuclear magnetic resonance (ssNMR) spectrum analysis or their combination. As mentioned below, the amorphous solid has an XRPD pattern without obvious diffraction characteristic peak.

As used herein, the term "crystal form" or "crystal" refers to any solid substance with order in three dimension. Contrary to the amorphous substance, it has characteristic XRPD pattern with peak(s) having clear boundaries.

As used herein, the term "substantially pure" means that based on the total amount of the compound of formula I, the content of crystal in the compound is about 95 wt % or more, preferably about 98 wt % or more, more preferably about 99 wt % or more.

As used herein, the term "X-ray powder diffraction pattern (XRPD pattern)" refers to diffraction pattern of experimental observation or parameters, data or value derived therefrom. An XRPD pattern is generally characterized by position of diffraction angle (x-axis) and/or intensity (y-axis).

As used herein, the term "2θ" refers to diffraction angle shown as degree)(° set in the X-ray diffraction experiments, which are generally x-axis unit of a diffraction pattern. If an incident beam is diffracted when it forms an angle theta (θ) with a certain lattice plane, the experimental setting needs to report the reflected beam with an angle 2 theta (2θ). It should be understood that reference herein to specific 2θ values for a specific crystal form is intended to mean the 2θ values (in degrees) as measured using the X-ray diffraction experimental conditions as described herein, for example, as described herein, using Cu-Kα irradiation radiation source. XRPD pattern herein is preferably collected on X'Pert$^3$ X ray powder diffraction analyzer in transmission mode at room temperature. The device uses Cu-Kα irradiation, and the scanning range is 2θ 3.5°-40°.

As used herein, the term "substantially identical" for an X-ray diffraction peak means that typical peak position and/or intensity variability are considered. For example, a person skilled in the art will appreciate that the diffraction angle (2θ) will show some variability, typically as much as 0.1 to 0.2 degree, and the apparatus for measuring the diffraction may also lead to some variability. Further, a person skilled in the art will appreciate that relative peak intensity will vary due to difference between apparatuses as well as degree of crystallinity, preferred orientation, prepared sample surface, and other factors known to a person skilled in the art, and should be deemed as qualitative measures only.

As used herein, the "the highest peak temperature of the endothermic peak" in the DSC curve of the crystal form means the peak value(s) representing the endothermic peak profile of the DSC curve. The highest peak temperature of the endothermic peak measured by DSC may vary depending on the purity, weight, particle size of the test article, and the test heating rate and system error of the apparatus. The provided values cannot be construed as absolute values (Reference: Guo Yonghui, Yang Ning, Lu Yang. Application of Differential Scanning calorimetry in the Research of Crystal Form Drugs [C]// China Crystal Form Drug R&D Technology Seminar. 2010).

It should be understood that depending on different types of equipment or different test conditions used, the DSC curve may vary slightly. For example, a Mettler Toledo DSC1 differential scanning calorimeter can be used to determine the DSC curve. As used herein, the term "substantially identical" for DSC curve will take into account representative characteristic peak positions. For example, a person skilled in the art will understand that the characteristic peak positions may show some variability, usually up to 5° C. For solid samples comprising polymorphs, the heating rate of the DSC test has a notable influence on the DSC curve. At a relatively fast heating rate, the thermal hysteresis effect of the instrument is obvious, and the solid crystal form with a high melting point does not get enough time for recrystallization. Therefore, the DSC curve often shows only the melting endothermic peak of the crystal form with a low melting point. At a moderate heating rate, the DSC curve shows two peaks: the melting endothermic peaks of the crystal form with a low melting point and the solid crystal form with a high melting point. Only at a relatively low heating rate, the thermal hysteresis effect of the instrument is weak, and three peaks would be shown: the melting peak of the crystal form with a low melting point-the exothermic peak of recrystallization-the melting endothermic peak of the crystal form with a high melting point. A person skilled in the art will understand that the determination of the range of heating rate corresponding to the above different DSC curves may vary depending on the weight, morphology, particle size and distribution of the test article (Reference: Giron D. Thermal analysis and calorimetric methods in the characterisation of polymorphs and solvates[J]. Thermochimica Acta, 1995, 248:1-59).

"Thermogravimetric Analysis (TGA)" is a common method for determining the thermal stability of compounds. The TGA curve can be measured, for example, on a Mettler Toledo TGA1 instrument. The error of TGA may be within about ±0.5 wt %. The term "substantially identical" means that such error variations are considered. Exemplary test conditions are: temperature range is 35-500° C., heating rate is 10 K/min, and purge gas is nitrogen (99.99%).

"Particle size detection" is a common method for determining particle size. The particle size can be measured, for example, on a Malvern Mastersizer 3000 laser particle size analyzer using Hydro LV injector. The particle size distribution can be denoted by Dv(10) (also called D10), Dv(50) (also called D50), Dv(90) (also called D90), etc. D50, also known as the median particle size, refers to the corresponding particle size when the cumulative particle size distribution percentage of the sample reaches 50%, and the particles with a size greater than and less than this value account for 50% in the sample, respectively. Similarly, the particle size value corresponding to D90 means that 90% of the particles in the sample have a particle size below this value. The particle size value corresponding to D10 means that 10% of the particles in the sample have a particle size below this value. The particle size of Crystal Form D can affect the endothermic peak position(s) in DSC. Such a change is within ±5° C. The particle size distribution of Crystal Form D is the original particle size distribution of Crystal Form D.

As used herein, the term "ester" refers to the ester having 3-10 carbon atom. The examples comprise but not limited to ethyl acetate, propyl acetate, isopropyl acetate, butyl acetate, amyl acetate or a combination thereof, preferable ethyl acetate, isopropyl acetate or a combination thereof.

As used herein, the term "ether" refers to the ether having 2-6 carbon atoms. The examples comprise but not limited to diethyl ether, isopropyl ether, tetrahydrofuran, 1,4-dioxane or a combination thereof, preferable tetrahydrofuran, 1,4-dioxane or a combination thereof.

As used herein, the term "alkane" refers to the alkane having 1-10 carbon atoms. The examples comprise but not limited to n-pentane, n-hexane, cyclohexane, n-heptane, octane or a combination thereof, preferable n-pentane, n-hexane, n-heptane or a combination thereof, more preferably n-pentane, n-hexane or a combination thereof.

As used herein, the term "arene" refers to the arene having 6-10 carbon atoms. The examples comprise but not limited to benzene, toluene, xylene or a combination thereof.

As used herein, the term "good solvent" refers to the solvent which provides higher solubility for a substance. A crystal form is desired from the said substance. The term "poor solvent" refers to the solvent used to precipitate the desired crystalline substance. For example, when a solid substance is dissolved in a "good solvent" to form a solution, adding a "poor solvent" thereto or adding the resulting solution to a "poor solvent" would precipitate the substance, so as to give the corresponding crystal form.

As used herein, the term "room temperature" refers to about 20-30° C., preferably about 25° C.

Crystal Form D of the compound of formula I

In an aspect, the invention provides a Crystal Form D of the compound of formula I, wherein the Crystal Form D has an XRPD pattern comprising peaks at diffraction angles (2θ) of about 4.9±0.2°, 6.0±0.2°, 12.5±0.2°, 18.3±0.2°, 18.9±0.2°, 21.0±0.2°, 23.8±0.2°.

In some embodiments, the Crystal Form D has an X-ray powder diffraction (XRPD) pattern comprising peaks at diffraction angles (2θ) of about 4.9±0.2°, 6.0±0.2°, 7.3±0.2°, 12.5±0.2°, 18.3±0.2°, 18.9±0.2°, 19.7±0.2°, 21.0±0.2°, 22.2±0.2°, 23.8±0.2°.

In some embodiments, the Crystal Form D has an XRPD pattern comprising peaks at diffraction angles (2θ) of about 4.9±0.2°, 6.0±0.2°, 12.5±0.2°, 14.7±0.2°, 15.6±0.2°, 17.1±0.2°, 18.3±0.2°, 18.9±0.2°, 21.0±0.2°, 23.8±0.2°, 24.9±0.2°.

In some embodiments, the Crystal Form D has an XRPD pattern comprising peaks at diffraction angles (2θ) of about 4.9±0.2°, 6.0±0.2°, 7.3±0.2°, 12.5±0.2°, 14.7±0.2°, 15.6±0.2°, 17.1±0.2°, 18.3±0.2°, 18.9±0.2°, 19.7±0.2°, 21.0±0.2°, 22.2±0.2°, 23.8±0.2°, 24.9±0.2°.

In some embodiments, the Crystal Form D has an XRPD pattern comprising peaks at diffraction angles (2θ) of about 4.1±0.2°, 4.9±0.2°, 6.0±0.2°, 6.2±0.2°, 8.7±0.2°, 9.8±0.2°, 10.1±0.2°, 12.5±0.2°, 13.4±0.2°, 14.0±0.2°, 14.7±0.2°, 15.6±0.2°, 17.1±0.2°, 17.9±0.2°, 18.3±0.2°, 18.5±0.2°, 18.9±0.2°, 19.9±0.2°, 21.0±0.2°, 21.3±0.2°, 21.8±0.2°, 22.7±0.2°, 23.4±0.2°, 23.8±0.2°, 24.9±0.2°.

In some embodiments, the Crystal Form D has an XRPD pattern comprising peaks at diffraction angles (2θ) of about 4.1±0.2°, 4.9±0.2°, 6.0±0.2°, 6.2±0.2°, 7.3±0.2°, 8.7±0.2°, 9.8±0.2°, 10.1±0.2°, 12.5±0.2°, 13.4±0.2°, 14.0±0.2°, 14.7±0.2°, 15.6±0.2°, 17.1±0.2°, 17.9±0.2°, 18.3±0.2°, 18.5±0.2°, 18.9±0.2°, 19.7±0.2°, 19.9±0.2°, 21.0±0.2°, 21.3±0.2°, 21.8±0.2°, 22.2±0.2°, 22.7±0.2°, 23.4±0.2°, 23.8±0.2°, 24.9±0.2°.

In further embodiments, the Crystal Form D has an XRPD pattern comprising peaks at the following diffraction angles (2θ) (Table 1):

TABLE 1

| 2θ (°) ± 0.2° | Inter-planar spacing (d spacing) | Intensity (%) |
|---|---|---|
| 4.12 | 21.45 | 30.67 |
| 4.92 | 17.96 | 72.20 |
| 6.03 | 14.65 | 100.00 |
| 6.21 | 14.21 | 26.64 |
| 7.29 | 12.12 | 43.60 |
| 8.65 | 10.21 | 11.61 |
| 9.88 | 8.95 | 12.48 |
| 10.10 | 8.75 | 11.31 |
| 10.96 | 8.06 | 15.54 |
| 11.58 | 7.64 | 3.30 |
| 12.01 | 7.37 | 20.93 |
| 12.49 | 7.08 | 46.70 |
| 13.16 | 6.72 | 24.39 |
| 13.37 | 6.62 | 12.79 |
| 13.99 | 6.33 | 8.28 |
| 14.70 | 6.02 | 27.41 |
| 14.92 | 5.93 | 10.09 |
| 15.56 | 5.69 | 74.95 |
| 17.08 | 5.19 | 10.65 |
| 17.87 | 4.96 | 24.24 |
| 18.26 | 4.85 | 48.79 |
| 18.49 | 4.79 | 48.61 |
| 18.86 | 4.70 | 15.52 |
| 19.66 | 4.51 | 38.46 |
| 19.94 | 4.45 | 59.74 |
| 20.35 | 4.36 | 5.51 |
| 20.96 | 4.23 | 63.12 |
| 21.33 | 4.16 | 18.37 |
| 21.82 | 4.07 | 23.33 |
| 22.19 | 4.00 | 36.20 |
| 22.75 | 3.91 | 12.69 |
| 23.35 | 3.81 | 28.83 |
| 23.77 | 3.74 | 70.32 |
| 24.10 | 3.69 | 21.17 |
| 24.53 | 3.63 | 10.02 |
| 24.92 | 3.57 | 24.63 |
| 26.20 | 3.40 | 7.41 |
| 26.93 | 3.31 | 21.27 |
| 27.30 | 3.26 | 9.06 |
| 27.57 | 3.23 | 7.54 |
| 28.33 | 3.15 | 7.32 |
| 28.73 | 3.10 | 5.97 |
| 29.53 | 3.02 | 17.57 |
| 29.99 | 2.98 | 6.88 |
| 31.61 | 2.83 | 8.54 |
| 32.04 | 2.79 | 2.51 |
| 33.34 | 2.69 | 3.33 |
| 34.37 | 2.61 | 1.16 |
| 34.64 | 2.59 | 2.19 |
| 37.15 | 2.42 | 4.39 |
| 38.17 | 2.36 | 6.92 |
| 39.00 | 2.31 | 7.22 |

In further embodiments, the Crystal Form D has an XRPD pattern comprising peaks at diffraction angles (2θ) which are substantially identical to those shown in FIG. 1. In yet further embodiments, the Crystal Form D has an XRPD pattern with peaks which are substantially identical to those shown in FIG. 1. In a yet further embodiment, the Crystal Form D has an XRPD pattern as shown in FIG. 1.

Figure 2:
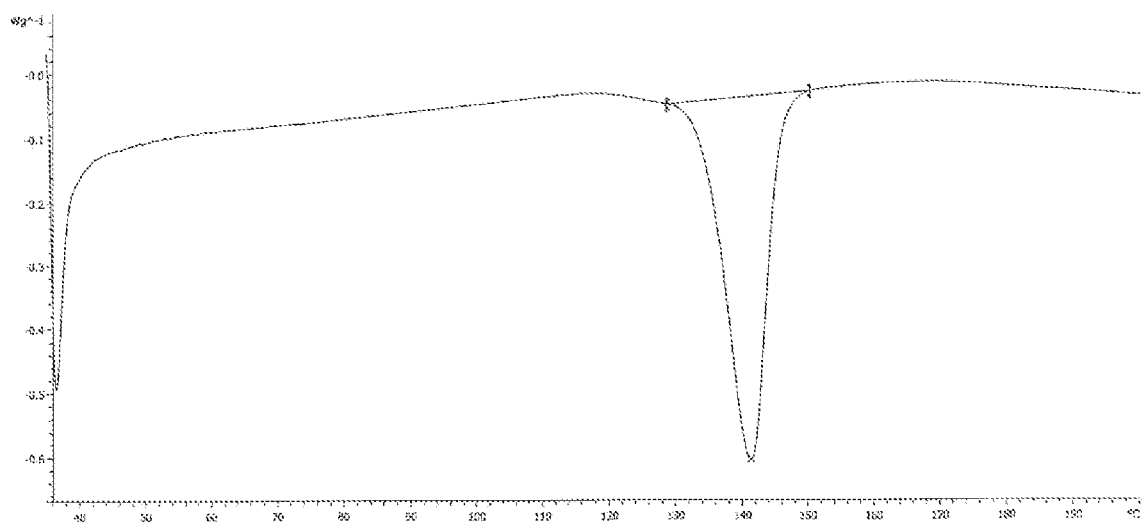
FIG. 2 shows the DSC curve of the Crystal Form D according to the invention (x-axis represents temperature (° C.), y-axis represents heat flow (W/g)).

In preferable embodiments, the Crystal Form D has a differential scanning calorimetry (DSC) curve comprising characteristic peaks at temperatures substantially identical to those shown in FIG. 2. In more preferable embodiments, the Crystal Form D has a DSC curve comprising characteristic peaks substantially identical to those shown in FIG. 2. In further preferable embodiments, the Crystal Form D has a DSC curve comprising characteristic peaks identical to those shown in FIG. 2.

In some embodiments, the Crystal Form D has a DSC comprising endothermic peak(s) with the highest peak temperature of about 138-145° C. In specific embodiments, the Crystal Form D has a DSC comprising endothermic peak(s) with the highest peak temperature of about 141° C.

Figure 3:
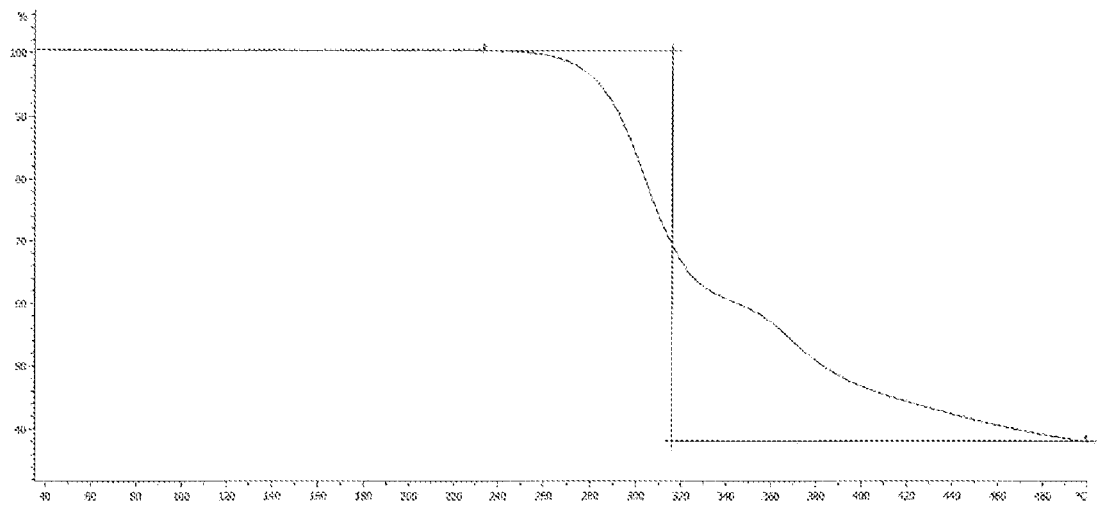
FIG. 3 shows the Thermogravimetric Analysis curve of the Crystal Form D according to the invention (x-axis represents temperature (° C.), y-axis represents weight percent (%)).

In some embodiments, the Crystal Form D has a TGA curve comprising weight loss profile substantially identical to that shown in FIG. 3. In preferable embodiments, the Crystal Form D has a TGA curve substantially as shown in FIG. 3. In more preferable embodiments, the Crystal Form D has a TGA curve as shown in FIG. 3.

In some embodiments, the Crystal Form D has a TGA curve showing that the Crystal Form D begins to decompose at about 225-235° C. In specific embodiments, the Crystal Form D has a TGA curve showing that the Crystal Form D begins to decompose at about 230° C. The Crystal Form D substantially has no weight loss before decomposition.

In some embodiments, the Crystal Form D has the following particle size distribution: Dv(10): about 2-3.5 μm, Dv(50): about 10-20 μm, Dv(90): about 40-60 μm. In specific embodiments, the Crystal Form D has the following particle size distribution: Dv(10): about 2.925 μm, Dv(50): about 15.360 μm, Dv(90): about 47.631 μm.

The Crystal Form D according to the invention is substantially pure.

Preparation Method of the Crystal Form D

In another aspect, the invention also provides a process for preparing the Crystal Form D of the compound of formula I.

In an embodiment of the process for preparing the Crystal Form D according to the invention, the process comprises 1) dissolving the compound of formula I as solid in a good solvent for crystallization, 2) adding the solution obtained in step 1) to a poor solvent for crystallization for crystallization, 3) separating the resulting product and optionally subjecting it to drying to give the Crystal Form D.

In some embodiments, the good solvent for crystallization in step 1) is selected from an ether solvent, an ester solvent and a mixture thereof. In some preferable embodiments, the good solvent for crystallization is an ether solvent or an ester solvent, more preferably an ether solvent.

In other embodiments, the poor solvent for crystallization in step 2) is selected from an alkane solvent, an arene solvent and a mixture thereof, preferably selected from an alkane solvent.

The ester solvent may be ethyl acetate, propyl acetate, isopropyl acetate, butyl acetate, amyl acetate or a combination thereof, preferably ethyl acetate, isopropyl acetate or a combination thereof.

The ether solvent may be diethyl ether, isopropyl ether, tetrahydrofuran, 1,4-dioxane or a combination thereof, preferably tetrahydrofuran, 1,4-dioxane or a combination.

The alkane solvent may be n-pentane, n-hexane, cyclohexane, n-heptane, octane or a combination thereof, preferably n-pentane, n-hexane, n-heptane or a combination thereof, more preferably n-pentane, n-hexane or a combination thereof.

The arene solvent may be benzene, toluene, xylene or a combination thereof.

In some more preferable embodiments, the good solvent for crystallization is an ether solvent, preferably tetrahydrofuran, 1,4-dioxane or a combination thereof, and the poor solvent for crystallization is an alkane solvent, preferably n-pentane, n-hexane, n-heptane or a combination thereof, more preferably n-pentane, n-hexane or a combination thereof.

In step 1), heating may be performed to promote dissolution of the compound of formula I. Unless stated otherwise, "heating" in the preparing process has no particular limitation for the temperature, provided it is lower than the boiling point of the solvent. Preferable heating temperature is 30-90° C., more preferably 35-85° C., for example, 40° C., 60° C., 80° C. This step can be performed at room temperature.

In some embodiments, in step 1), ratio of the weight of the added compound of formula I as solid to the volume of the good solvent for crystallization (w/v) is about 1:1-1:10, preferably about 1:3-1:5, e.g. 1:3.3, 1:3, 1:5.

In some embodiments, volume ratio of the good solvent for crystallization to the poor solvent for crystallization is about 1:20-20:1, preferably about 1:1-1:10, more preferably about 1:3-1:8, further preferably about 1:4-1:7, e.g. 1:4, 1:6, 1:6.7.

In some embodiments, the "adding" in step 2) is performed dropwise.

In other embodiments, the "adding" in step 2) is performed in one portion.

In preparing process according to the invention, a seed crystal may be optionally added. Addition of the seed crystal may reduce the time of crystallization to some extent. Type and amount of the added seed crystal are such that can facilitate the crystallization of the compound of formula I to form the desired crystal form.

In some embodiments, in step 2), a seed crystal of the Crystal Form D is optionally added to the poor solvent for crystallization. The amount added can be about 0.01-5 (w/w) %, preferably 0.03-2 (w/w) %, e.g. about 1 (w/w) %, 0.33 (w/w) %. The w/w means weight percentage of the Crystal Form D and the compound of formula I.

After step 2), stirring can be optionally performed for crystallization. Unless stated otherwise, there is no particular limitation for speed and time of "stirring", provided that the agents can be mixed uniformly.

Unless stated otherwise, crystallization can occur at any step of the preparing process, for example, it may be performed at the same time as stirring.

The prepared crystal form can be separated and recovered by the processes including decantation, centrifugation, evaporation, gravity filtration, suction filtration, or any other technology for solid separation under increased or reduced pressure, preferably by filtration separation.

There is no particular limitation for the "drying" conditions of the process for preparing the new crystal form of the compound of formula I. The "drying" herein is performed preferably under reduced pressure and more preferably in vacuum, at any temperature, preferably room temperature, until the levels of residual solvents are reduced to within the limits given in International Conference on Harmonisation of Technical Requirements for Registration of Pharmaceuticals for Human Use ("ICH") guideline. Depending on types of the solvents, the levels of residual solvents may vary, but not over about 5000 ppm, or preferably about 4000 ppm, or more preferably about 3000 ppm. Drying can be performed in fluidized bed dryer, rotary vacuum dryer, spin flash dryer, tray drier, vacuum oven, air oven, flash dryer or the like. Drying can be performed at about 100° C. or lower, about 80° C. or lower, about 60° C. or lower, about 50° C. or lower, about 30° C. or lower, or at any other suitable temperature, under atmosphere or reduced pressure (preferably vacuum), for any time sufficient (e.g. about 1, 2, 3, 5, 10, 15, 20, 24 hours or overnight) to achieve the desired result. Drying can be performed for any desired times to give the product with desired attributes.

In some preferable embodiments, the process for preparing the Crystal Form D according to the invention comprises, 1) dissolving the compound of formula I as solid in an ether or ester solvent, 2) adding the solution obtained in step 1) to an alkane solvent dropwise for crystallization, 3) separating the resultant product and optionally subjecting it to drying to give the Crystal Form D.

In some more preferable embodiments, the process for preparing the Crystal Form D according to the invention comprises, 1) dissolving the compound of formula I as solid in an ether solvent, 2) adding the solution obtained in step 1) to an alkane solvent dropwise for crystallization, 3) separating the resulting product and optionally subjecting it to drying to give the Crystal Form D.

In some embodiments, the volume ratio of the ether solvent to the alkane solvent is about 1:20-20:1, preferably about 1:1-1:10, more preferably about 1:3-1:8, further preferably about 1:4-1:7.

In other embodiments, step 2) further comprises a step of adding seed crystal of the Crystal Form D. The amount of the added seed crystal of the Crystal Form D may be about 0.01-5 (w/w) %, preferably 0.03-2 (w/w) %, e.g. about 1 (w/w) %, 0.33 (w/w) %.

In the above-mentioned processes, the ether solvent may be diethyl ether, isopropyl ether, tetrahydrofuran, 1,4-dioxane or a combination thereof, preferably tetrahydrofuran, 1,4-dioxane or a combination thereof.

In the above-mentioned processes, the alkane solvent may be n-pentane, n-hexane, cyclohexane, n-heptane, octane or a combination thereof, preferably n-pentane, n-hexane, n-heptane or a combination thereof, more preferably n-pentane, n-hexane or a combination thereof.

The Crystal Form D obtained by the process according to the invention is substantially pure.

Pharmaceutical Composition and Use

In some embodiments, the invention provides a pharmaceutical composition, comprising the Crystal Form D according to the invention and one or more pharmaceutically acceptable carriers.

In an aspect, the invention provides a use of the Crystal Form D according to the invention or the pharmaceutical composition according to the invention for the manufacture of a medicament for preventing or treating thrombocytopenia.

In another aspect, the invention provides the Crystal Form D according to the invention or the pharmaceutical composition according to the invention for use in preventing or treating thrombocytopenia.

In yet another aspect, the invention provides a method for preventing or treating thrombocytopenia, comprising administering to a subject in need thereof the Crystal Form D according to the invention or the pharmaceutical composition according to the invention in an effective amount.

The thrombocytopenia herein comprises blood diseases with abnormal platelet count such as thrombocytopenia after hematopoietic stem cell transplantation (bone marrow transplantation etc.), thrombocytopenia after chemotherapy, aplastic anemia, myelodysplastic syndrome, acquired thrombocytopenia such as idiopathic thrombocytopenic purpura or the like, congenital thrombocytopenia such as thrombopoietin defects or the like, viral pneumonia (hepatitis C, etc.), other hepatic diseases (liver cirrhosis, etc.), or the like. For example, prevention and treatment can be applied to thrombocytopenia due to administration of anti-cancer agents against hematopoietic organ tumor, solid tumor, or the like. They can be used as therapeutic agents for thrombocytopenia due to administration of anti-cancer agents and can be used as prophylaxis agents when the anti-cancer agents are expected to result in thrombocytopenia. They can be used as therapeutic agents and/or prophylaxis agents when platelets are expected to be reduced upon cardiovascular system (heart and blood vessel etc.) surgical operations.

The term "pharmaceutically acceptable carrier" used herein refers to the diluent, vehicle, excipient, or medium which is co-administered with the therapeutic agent, and are within the scope of reliable medical judgment, suitable for contact with human and/or animal tissues, without undue toxicity, irritation, allergic reaction or other problems or complications and has acceptable benefit/risk ratio.

The pharmaceutically acceptable carriers which can be used in the pharmaceutical composition according to the invention comprise but not limited to sterile liquid, for example water and oil, including those derived from petroleum, animals, vegetables or synthetic origin, e.g. soybean oil, peanut oil, mineral oil or the like. When the pharmaceutical composition is intravenously administered, water is exemplary carrier. Normal saline and glucose and glycerin aqueous solution can be used as liquid carriers, especially for injection. Suitable pharmaceutical excipients comprise glucose, starch, lactose, gelatin, maltose, sucrose, chalk, silica gel, glycerin monostearate, sodium stearate, talcum, sodium chloride, glycerin, propanediol, water, ethanol or the like. The composition if necessary, may comprise small amount of wetting agent, emulsifying agent or pH buffering agent. Oral formulation may comprise standard carrier, e.g. mannitol, lactose, starch, magnesium stearate, cellulose, saccharin sodium, magnesium carbonate or the like in pharmaceutical grade. Examples of suitable pharmaceutically acceptable carriers can be found in e.g. Remington's Pharmaceutical Sciences (1990).

The composition according to the invention can act systemically and/or topically. To this end, it can be administered through a suitable route, such as through injection, intraarterial, subcutaneous, intravenous, intraperitoneal, intramuscular or transdermal administration, or administered orally, nasally, buccally, transmucosally, topically, as an ophthalmic formulation, or via inhalation.

For these administration routes, the pharmaceutical composition can be administered by suitable dosage forms. The dosage forms comprise but not limited to tablet, capsule, troche, hard candy, powder, spray, cream, ointment, suppository, gel, aqueous suspension, injection, elixir, syrup.

The pharmaceutical composition according to the invention can be prepared by any processes well known in the art, for example by mixing, dissolving, granulating, sugar coating milling, emulsifying, freeze-drying or the like. The term "therapeutically effective amount" refers to those of the compounds after administration will relieve one or more symptoms of the diseases to be treated to some extent.

Dosage regimens can be adjusted to provide the desired optimal response. For example, a single bolus can be administered, several divided doses can be administered over time, or the dose can be proportionally reduced or increased as indicated by the exigencies of the therapeutic situation. It is to be noted that dosage values can vary with the type and severity of the condition to be alleviated, and can include single or multiple doses. It is to be further understood that for any particular subject, specific dosage regimens should be adjusted over time according to the individual need and the professional judgment of the person administering or supervising the administration of the composition.

The administered amount of the compounds according to the invention will depend on the individual to be treated, severity of the disorder or condition, rate of administration, formulation of the compounds and the discretion of the prescribing physician. Generally, an effective dosage is about 0.0001 to about 100 mg per kg body weight per day, for example, about 0.01 to about 10 mg/kg/day, in single or divided doses. For a human of 70 kg, total amount is about 0.007 mg/day to about 7000 mg/day, for example about 0.7 mg/day to about 700 mg/day. In some cases, a dosage level no more than the lower limit of the above ranges may be sufficient; while in other cases, larger doses can still be employed without causing any harmful side effect, provided that such larger doses are first divided into several small doses for administration throughout the day.

The content or used amount of the compounds according to the invention in the pharmaceutical composition may be about 0.01 mg to about 1000 mg, suitably 0.1-500 mg, preferably 0.5-300 mg, more preferably 1-150 mg, particularly preferably 1-50 mg, e.g. 1.5 mg, 2 mg, 4 mg, 10 mg, 25 mg or the like.

Unless stated otherwise, as used herein, the term "treating" refers to reversing, alleviating, inhibiting the disorder or condition for this term or development of one or more symptoms of such disorder or condition, or preventing the disorder or condition or one or more symptoms of such disorder or condition.

The term "individual" used herein comprises human or non-man animal. An exemplary human subject includes a human (referred to as a patient) subject having a disease (such as one described herein), or a normal subject. The term "non-human animal" comprises all vertebrates, for example non-mammals (e.g. amphibians, reptiles, birds) and mammals, for example non-human primates, livestock and/or domestic animals (e.g. dogs, cats, sheep, cows, pigs or the like).

Beneficial Effects

The advantages of the Crystal Form D according to the invention comprise but not limited to high solubility, good stability, and good pharmacokinetic properties, applicability for preparation into pharmaceutical formulation. The process for preparing the crystal form is simple and effective and is suitable for scaled production.

Specifically, the Crystal Form D according to the invention has good physical properties, comprising but not limited to solubility, dissolution, light resistance, low hygroscopicity, high temperature resistance, high humidity resistance, stability, fluidity and significantly improved viscidity or the like.

For example, the Crystal Form D according to the invention can significantly reduce the filtration time, shorten the production time and save the cost during formulation preparation. The Crystal Form D according to the invention has good photostability, ensuring the reliability during storage and transportation, whereby ensuring the formulation safety. The crystal form does not require particular packaging handling to prevent the influence of light, whereby reducing the cost. The crystal form does not decompose due to light, increasing the formulation safety and effectiveness after long-term storage. The patient using the crystal form will be free of photosensitized reaction of the formulation due to exposure to the sunlight.

The Crystal Form D according to the invention undergoes little or no decomposition during storage or transportation at environmental temperature. The DSC analysis of the crystal form shows that melting or desolvation happens over 50° C. The crystal form exhibits good thermostability and long-term stability, suggesting applicability for standard formulation process.

The Crystal Form D according to the invention shows good chemical and physical stability, ease of preparation and improved suitability for formulation preparation. For example, the Crystal Form D according to the invention can be milled into fine powders, screened with 100 μm and 50 μm filtering screens. The milled Crystal Form D has an XRPD pattern identical to that before milling.

The Crystal Form D according to the invention shows good efficacy in preventing or treating blood diseases associated with abnormal platelet count, such as thrombocytopenia. It can maintain sufficient bioactivity and provide effective therapeutical dosage of the compound of formula I in vivo.

The Crystal Form D according to the invention is suitable and convenient for scaled production, and the formulation obtained therefrom can reduce irritation and enhance absorption, which address the issues in metabolism rate, significantly lower the toxicity, improve the safety and effectively ensure the quality and performance of the formulation.

EXAMPLE

The invention will be further illustrated by the following Examples, of which the purpose is for understanding of the invention.

Preparation and Characterization of Crystal Form D of the Compound of Formula I

Device and Method

X-Ray Powder Diffraction (XRPD)

XRPD pattern is collected on X'Pert³ X ray powder diffraction analyzer in transmission mode at room temperature. The device uses Cu-Kα irradiation, scanning voltage is 40 kV, current is 40 mA, increment is 0.013°, counting time for each increment is 50 s, scanning range is 2θ 3.5°-40°.

Differential Scanning Calorimetry (DSC)

DSC is collected on Mettler Toledo DSC1 differential scanning calorimeter, heating rate of the DSC device is 10K/min.

Thermogravimetric Analysis (TGA)

TGA is collected on Mettler Toledo TGA1 Thermogravimetric Analyzer, purge gas is N2 (99.99%), 100 ml/min; heating rate: 10K/min; temperature range: 35-500° C.

Particle Size Analysis

Particle size analysis is performed on Malvern Mastersizer 3000 laser particle size analyzer with Hydro LV injector.

Example 1

3 g of the compound of formula I was weighed in a container, to which was added 10 ml of tetrahydrofuran. Stirring was conducted to dissolution. At room temperature, to another container was added 1 (w/w) % of seed crystal of Crystal Form D and 60 ml of n-pentane with stirring. A solution of the compound of formula I in tetrahydrofuran was added dropwise into the n-pentane container with stirring for crystallization. Filtration and drying were performed to give the Crystal Form D.

XRPD analysis was performed on the obtained Crystal Form D and the XRPD pattern was shown in FIG. 1 and the relevant data was shown in Table 1.

Particle size determination was performed on the Crystal Form D. The Crystal Form D has the following particle size distribution: Dv(10): 2.925 μm, Dv(50): 15.360 μm, Dv(90): 47.631 μm.

DSC determination was performed on the Crystal Form D and the resulting DSC curve was shown in FIG. 2. In the curve, initiating temperature (Onset) and the highest peak temperature (Peak) of the endothermic peak of the sample were about 134° C. and 141° C., respectively, the end melting temperature (Endset) was about 145° C.

TGA determination was performed on the Crystal Form D and the resulting TGA curve was shown in FIG. 3. In the curve, the sample began to decompose at about 230° C. and no weight loss was found before decomposition.

Example 2

1 g of compound of formula I was weighed in a container, to which was added 3 ml of tetrahydrofuran. Stirring was conducted to dissolution. At room temperature, to another container was added 20 ml of n-hexane and 1 (w/w) % of seed crystal of the Crystal Form D of the compound of formula I with stirring. A solution of the compound of formula I in tetrahydrofuran was added dropwise into the n-hexane container with stirring for crystallization. Filtration and drying were performed. The obtained crystal form has XRPD pattern and DSC curve substantially identical to those of Example 1, indicating obtaining the Crystal Form D.

Example 3

1 g of compound of formula I was weighed in a container, to which was added 3 ml of tetrahydrofuran. Stirring was conducted to dissolution. At room temperature, to another container was added 20 ml of n-heptane and 1 (w/w) % of seed crystal of the Crystal Form D of the compound of formula I with stirring. A solution of the compound of formula I in tetrahydrofuran was added dropwise into the n-heptane container with stirring for crystallization. Filtration and drying were performed. The obtained crystal form has XRPD pattern and DSC curve substantially identical to those of Example 1, indicating obtaining the Crystal Form D.

Example 4

1 g of compound of formula I was weighed in a container, to which was added 5 ml of 1,4-dioxane. Stirring was conducted to dissolution. At room temperature, to another container was added 20 ml of n-pentane and 1 (w/w) % of seed crystal of the Crystal Form D of the compound of formula I with stirring. A solution of the compound of formula I in 1,4-dioxane was added dropwise into the n-pentane container with stirring for crystallization. Filtration and drying were performed. The obtained crystal form has XRPD pattern and DSC curve substantially identical to those of Example 1, indicating obtaining the Crystal Form D.

Example 5

1 g of compound of formula I was weighed in a container, to which was added 5 ml of 1,4-dioxane. Stirring was conducted to dissolution. At room temperature, to another container was added 20 ml of n-hexane and 1 (w/w) % of seed crystal of the Crystal Form D of the compound of formula I with stirring. A solution of the compound of formula I in 1,4-dioxane was added dropwise into the n-hexane container with stirring for crystallization. Filtration and drying were performed. The obtained crystal form has XRPD pattern and DSC curve substantially identical to those of Example 1, indicating obtaining the Crystal Form D.

Experimental Example 1: Solubility Test

In this Experimental Example, the solubility of two crystal form in different pH of simulated human gastric juice were tested to study the solubility of the crystal forms.

Solubility test: HPLC external standard method

Chromatographic column: octadecyl silane bonded silica gel as filler

Mobile phase: phosphate buffer (pH3.5):methanol:acetonitrile=2:9:9 (volume ratio)

Detection wavelength: 215 nm

Excess amount of Crystal Form D and Crystal Form Y were placed in tubes with plug, to which were added 10 ml of water (purified water), hydrochloric acid solution of pH 1.2, hydrochloric acid solution of pH 2.0, acetate buffer of pH 4.0, phosphate buffers of pH 4.5, 5.0, 6.8, 8.0, respectively, and vibrated on 37° C. water bath, then filtered. The subsequent filtrate was subjected to HPLC assay.

The preparations of various pH buffers can be referred to "Guideline for Dissolution Test of Normal Oral Solid Formulation" issued by Center for Drug Evaluation of China Food and Drug Administration for dissolution medium, and are detailed as follows:

The hydrochloric acid solution of pH 1.2 is prepared by diluting 7.65 ml of hydrochloric acid with water to 1000 ml and mixing well.

The hydrochloric acid solution of pH 2.0 is prepared by diluting 1.17 ml of hydrochloric acid with water to 1000 ml and mixing well.

The acetate buffer of pH 4.0 is prepared by diluting mixture of 1.22 g of sodium acetate with 20.5 ml of 2 mol/L acetic acid solution with water to 1000 ml and mixing well. The 2 mol/L acetic acid solution is prepared by diluting 114 mL of glacial acetic acid with water to 1000 ml.

The phosphate buffers of pH 4.5, 5.0, 6.8, 8.0 are prepared by adjusting pH of 0.2 mol/L monopotassium phosphate solution with 0.2 mol/L sodium hydroxide solution to pH 4.5, 5.0, 6.8, 8.0, respectively. The 0.2 mol/L monopotassium phosphate solution is prepared by dissolving 27.22 g of monopotassium phosphate in water and diluting to 1000 mL. The 0.2 mol/L sodium hydroxide solution is prepared by dissolving 8.00 g of sodium hydroxide in water and diluting to 1000 mL.

TABLE 2

| pH or water | 1.2 | 2.0 | 4.0 | 4.5 | 5.0 | 6.8 | 8.0 | water |
|---|---|---|---|---|---|---|---|---|
| Solubility of two crystal forms in various pH solution or water/(μg/ml) | | | | | | | | |
| Crystal Form Y | 0.7616 | 0.4915 | 0.4327 | 0.5623 | 0.6993 | 3.2046 | 43.0713 | 5.2325 |
| Crystal Form D | 19.1353 | 14.5872 | 10.6478 | 11.4829 | 13.8229 | 36.0017 | 110.5589 | 41.3607 |

As shown in Table 2, solubility of two crystal forms in simulated human gastric juice with various pH are tested and the Crystal Form D according to the invention showed solubility significantly better than that of Crystal Form Y.

Experimental Example 2: Stability Test

In this Experimental Example, high temperature, high humidity tests were used to study the chemical stability of the crystal form according to the invention.

Purity test: HPLC method (Chinese Pharmacopoeia 2015, Volume IV, general principles 0512)

Chromatographic column: octadecyl silane bonded silica gel as filler

Mobile phase A: 0.02 mol/L phosphate buffer (pH 3.0)-methanol-acetonitrile

Mobile phase B: methanol-acetonitrile-water

Detection wavelength: 215 nm.

Elution condition: gradient elution

Weight loss on drying assay: Chinese Pharmacopoeia 2015, Volume IV, general principles 0831

Experimental Example 2-1: High Temperature Stability Test

The Crystal Form D of the compound of formula I was placed in a sealed and clean glass bottle and placed in 60° C. constant temperature oven. Samples were taken 10 day/30 day respectively for impurity content determination. The purity change was shown in Table 3 and XRPD was shown in FIG. 4.

TABLE 3

High temperature stability data of Crystal Form D

| Time | Purity Change |
|---|---|
| 10 day | 0.04% |
| 30 day | 0.03% |

Note: Purity Change=(Difference of sample purity at day 0 and sample purity after a certain period)/Sample purity at day 0×100%.

Figure 4:
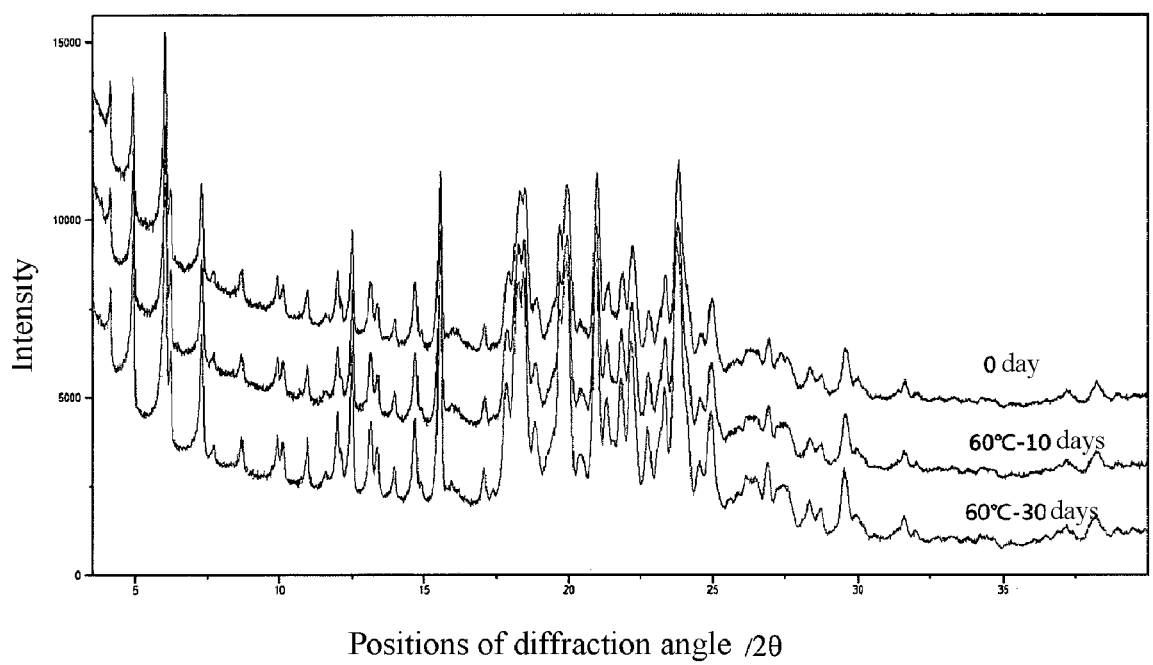
FIG. 4 shows the XRPD pattern of the Crystal Form D according to the invention before and after high temperature stability test (x-axis represents position of diffraction angle 2θ (°), y-axis represents intensity of diffraction).

As can be seen from Table 3 and FIG. 4, the Crystal Form D did not show obvious change in purity and no change in crystal form under high temperature condition, indicating high temperature stability.

Experimental Example 2-2: High Humidity Stability Test

The Crystal Form D of the compound of formula I was spread in open petri dish with thickness ≤5 mm, at room temperature, in constant temperature incubator of relative humidity (RH) 92.5%. Samples were taken 10 day/30 day for impurity content determination. The purity change and weight loss on drying were shown in Table 4 and XRPD was shown in FIG. 5.

TABLE 4

High humidity stability data of Crystal Form D

| Time | Purity Change | Weight loss on drying |
|---|---|---|
| 0 day | — | 0.31% |
| 10 day | 0.05% | 0.35% |
| 30 day | 0% | 0.36% |

Figure 5:
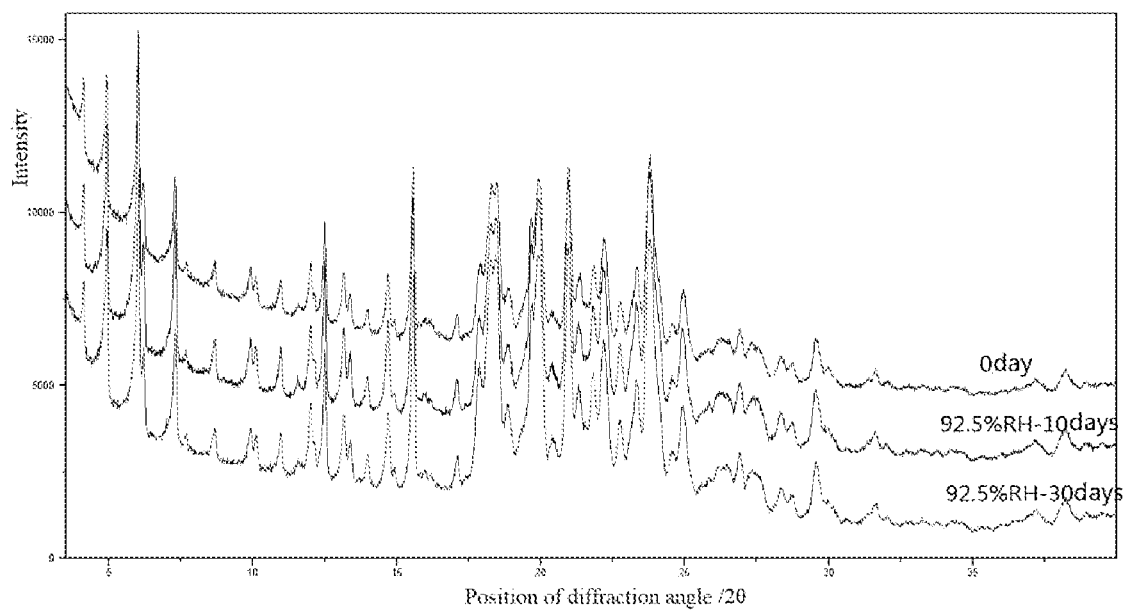
FIG. 5 shows the XRPD pattern of the Crystal Form D according to the invention before and after high humidity stability test (x-axis represents position of diffraction angle 2θ (°), y-axis represents intensity of diffraction).

As can be seen from Table 4 and FIG. 5, the Crystal Form D did not show obvious change in purity, little change in weight loss on drying and no change in crystal form under high humidity condition, indicating high humidity stability.

Experimental Example 2-3: Long-Term and Accelerated Stability Test

The Crystal Form D of the compound of formula I was packed with inner bag (pharmaceutical low density polyethylene bag) and outer bag (pharmaceutical polyester/aluminum/polyethylene composite film bag), placed under the following stability testing conditions for stability tests. Chemical purity data was shown in Table 5, XRPD was used to study crystal form change and was shown in FIG. 6.

TABLE 5

Long-term and accelerated stability data of Crystal Form D

| Testing condition | Accelerated (40° C. ± 2° C./ RH75% ± 5%) | Long-term (30° C. ± 2° C./ RH65% ± 5%) | Long-term (25° C. ± 2° C./ RH60% ± 5%) |
|---|---|---|---|
| 0 day | 99.83% | 99.83% | 99.83% |
| 6 month | 99.83% | 99.83% | 99.83% |

Figure 6:
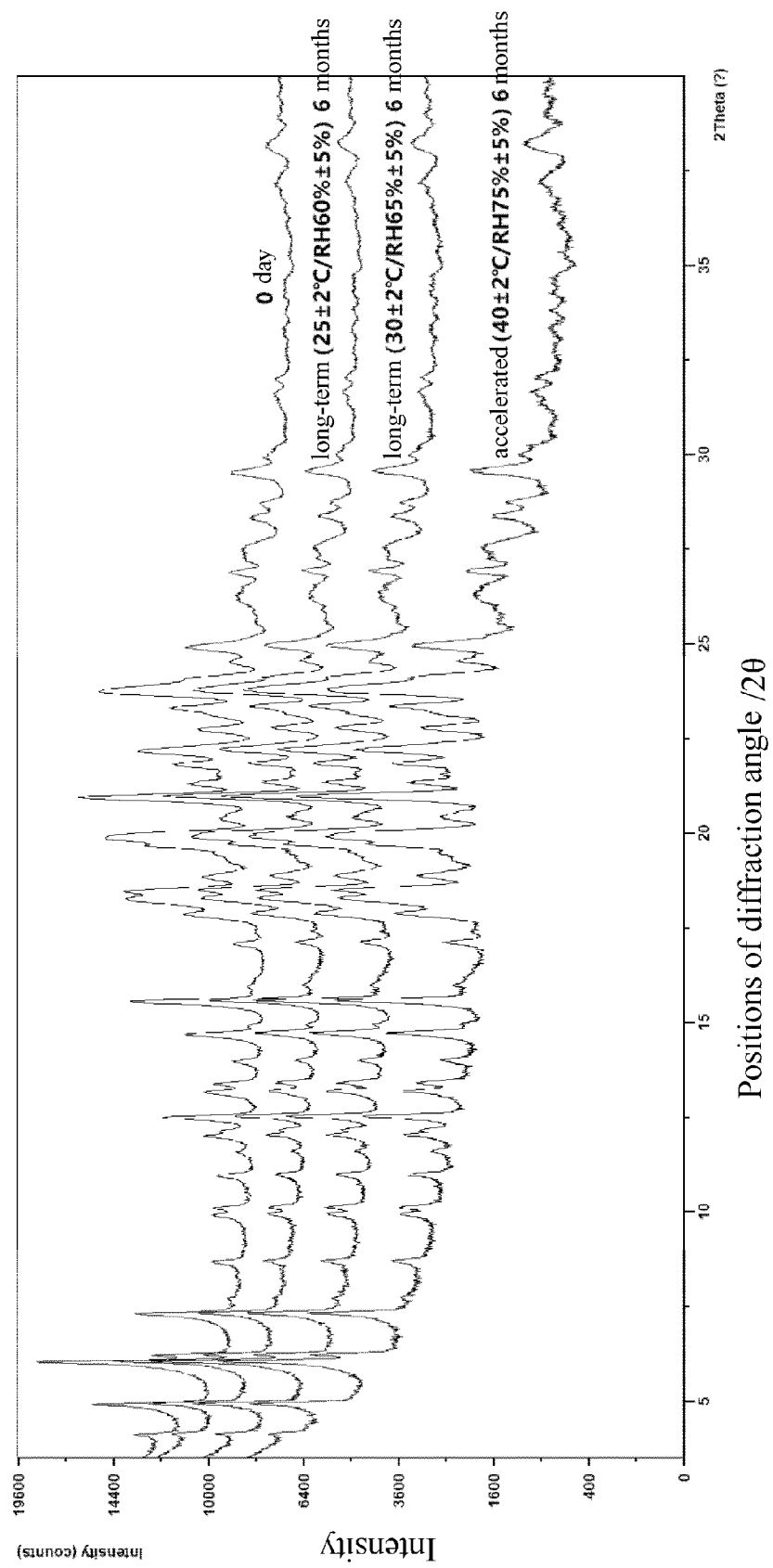
FIG. 6 shows the XRPD pattern of the Crystal Form D according to the invention before and after long-term and accelerated stability test (x-axis represents position of diffraction angle 2θ (°), y-axis represents intensity of diffraction).

As can be seen from Table 5 and FIG. 6, the Crystal Form D, after 6 month or more under long-term and accelerated conditions, showed no change in purity or crystal form, indicating good stability.

Experimental Example 3: Pharmacokinetic Study

The Crystal Form D of the compound of formula I was administered to dogs, mice and monkeys to study the pharmacokinetic properties of the Crystal Form D. The results showed that the Crystal Form D of the compound of formula I has good pharmacokinetic properties.

It will be understood by a person skilled in the art that many amendments and modifications can be done to the present invention without departing its spirits and scope. The embodiments described herein are only provided as examples and should not be construed as limitation. The true scope and spirits are defined by the claims and the description and examples are illustrative only.

The invention claimed is:

1. A Crystal Form D of a compound of formula I, characterized in that, the Crystal Form has an X-ray powder diffraction pattern comprising peaks at diffraction angles (2θ) of about 4.9±0.2°, 6.0±0.2°, 12.5±0.2°, 18.3±0.2°, 18.9±0.2°, 21.0±0.2°, 23.8±0.2°

I

2. The Crystal Form D according to claim 1, characterized in that,
the Crystal Form has an X-ray powder diffraction pattern comprising peaks at diffraction angles (2θ) of about 4.9±0.2°, 6.0±0.2°, 7.3±0.2°, 12.5±0.2°, 18.3±0.2°, 18.9±0.2°, 19.7±0.2°, 21.0±0.2°, 22.2±0.2°, 23.8±0.2°.

3. The Crystal Form D according to claim 1, characterized in that,
the Crystal Form has an X-ray powder diffraction pattern comprising peaks at diffraction angles (2θ) of about 4.9±0.2°, 6.0±0.2°, 12.5±0.2°, 14.7±0.2°, 15.6±0.2°, 17.1±0.2°, 18.3±0.2°, 18.9±0.2°, 21.0±0.2°, 23.8±0.2°, 24.9±0.2°.

4. The Crystal Form D according to claim 1, characterized in that,
the Crystal Form has an X-ray powder diffraction pattern comprising peaks at diffraction angles (2θ) of about 4.9±0.2°, 6.0±0.2°, 7.3±0.2°, 12.5±0.2°, 14.7±0.2°, 15.6±0.2°, 17.1±0.2°, 18.3±0.2°, 18.9±0.2°, 19.7±0.2°, 21.0±0.2°, 22.2±0.2°23.8±0.2°, 24.9±0.2°.

5. The Crystal Form D according to claim 1, characterized in that,
the Crystal Form has an X-ray powder diffraction pattern comprising peaks at diffraction angles (2θ) of about 4.1±0.2°, 4.9±0.2°, 6.0±0.2°, 6.2±0.2°, 8.7±0.2°, 9.8±0.2°, 10.1±0.2°, 12.5±0.2°, 13.4±0.2°, 14.0±0.2°, 14.7±0.2°, 15.6±0.2°, 17.1±0.2°, 17.9±0.2°, 18.3±0.2°, 18.5±0.2°, 18.9±0.2°, 19.9±0.2°, 21.0±0.2°, 21.3±0.2°, 21.8±0.2°, 22.7±0.2°, 23.4±0.2°, 23.8±0.2°, 24.9±0.2°.

6. The Crystal Form D according to claim 1, characterized in that,
the Crystal Form has an X-ray powder diffraction pattern comprising peaks at diffraction angles (2θ) of about 4.1±0.2°, 4.9±0.2°, 6.0±0.2°, 6.2±0.2°, 7.3±0.2°, 8.7±0.2°, 9.8±0.2°, 10.1±0.2°, 12.5±0.2°, 13.4±0.2°, 14.0±0.2°, 14.7±0.2°, 15.6±0.2°, 17.1±0.2°, 17.9±0.2°, 18.3±0.2°, 18.5±0.2°, 18.9±0.2°, 19.7±0.2°, 19.9±0.2°, 21.0±0.2°, 21.3±0.2°, 21.8±0.2°, 22.2±0.2°, 22.7±0.2°, 23.4±0.2°, 23.8±0.2°, 24.9±0.2°.

7. The Crystal Form D according to claim 1, characterized in that,
the Crystal Form has an X-ray powder diffraction pattern comprising peaks at diffraction angles (2θ) which are substantially identical to those shown in FIG. 1.

8. A process for preparing the Crystal Form D according to claim 1, comprising
1) dissolving the compound of formula I as solid in a good solvent for crystallization,
2) adding the solution obtained in step 1) to a poor solvent for crystallization for crystallization, 3) separating the resulting product and optionally subjecting it to drying to give the Crystal Form D,
wherein
the good solvent for crystallization is selected from an ether solvent, an ester solvent and a mixture thereof, and
the poor solvent for crystallization is selected from an alkane solvent, an arene solvent and a mixture thereof.

9. The process according to claim 8, characterized in that, the volume ratio of the good solvent for crystallization to the poor solvent for crystallization is about 1:20-20:1.

10. The process according to claim 8, characterized in that,
the good solvent for crystallization is an ether solvent or an ester solvent,
the poor solvent for crystallization is an alkane solvent.

11. The process according to claim 8, characterized in that, the ester solvent is selected from ethyl acetate, propyl acetate, isopropyl acetate, butyl acetate, amyl acetate and a combination thereof;
the ether solvent is selected from diethyl ether, isopropyl ether, tetrahydrofuran, 1,4-dioxane and a combination thereof;
the alkane solvent is selected from n-pentane, n-hexane, cyclohexane, n-heptane, octane and a combination thereof;
the arene solvent is selected from benzene, toluene, xylene and a combination thereof.

12. A pharmaceutical composition, comprising the Crystal Form D according to claim 1 and one or more pharmaceutically acceptable carriers.

13. A method for treating thrombocytopenia, comprising administering a subject in need thereof the Crystal Form D according to claim 1 in an effective amount.

14. A method for treating thrombocytopenia, comprising administering a subject in need thereof the pharmaceutical composition according to claim 12 in an effective amount.

15. A pharmaceutical composition, comprising the Crystal Form D according to claim 6 and one or more pharmaceutically acceptable carriers.

16. A pharmaceutical composition, comprising the Crystal Form D according to claim 7 and one or more pharmaceutically acceptable carriers.

17. A method for treating thrombocytopenia, comprising administering a subject in need thereof the Crystal Form D according to claim 6 in an effective amount.

18. A method for treating thrombocytopenia, comprising administering a subject in need thereof the Crystal Form D according to claim 7 in an effective amount.

19. A method for treating thrombocytopenia, comprising administering a subject in need thereof the pharmaceutical composition according to claim 15 in an effective amount.

20. A method for treating thrombocytopenia, comprising administering a subject in need thereof the pharmaceutical composition according to claim 16 in an effective amount.

21. The Crystal Form D according to claim 7, characterized in that,
the Crystal Form has an X-ray powder diffraction pattern with peaks which are substantially identical to those shown in FIG. 1.

22. The Crystal Form D according to claim 7, characterized in that,
the Crystal Form has an X-ray powder diffraction pattern as shown in FIG. 1.

23. The process according to claim 9, characterized in that,
   the volume ratio of the good solvent for crystallization to the poor solvent for crystallization is about 1:1-1:10.

24. The process according to claim 9, characterized in that,
   the volume ratio of the good solvent for crystallization to the poor solvent for crystallization is about 1:3-1:8.

25. The process according to claim 9, characterized in that,
   the volume ratio of the good solvent for crystallization to the poor solvent for crystallization is about 1:4-1:7.

26. The process according to claim 10, characterized in that, the good solvent for crystallization is an ether solvent.

27. The process according to claim 11, characterized in that,
   the ester solvent is selected from ethyl acetate, isopropyl acetate and a combination thereof;
   the ether solvent is selected from tetrahydrofuran, 1,4-dioxane and a combination thereof; and
   the alkane solvent is selected from n-pentane, n-hexane, n-heptane and a combination thereof.

28. The process according to claim 27, characterized in that, the alkane solvent is selected from n-pentane, n-hexane and a combination thereof.

* * * * *

UNITED STATES PATENT AND TRADEMARK OFFICE
CERTIFICATE OF CORRECTION

PATENT NO. : 11,174,234 B2
APPLICATION NO. : 17/053893
DATED : November 16, 2021
INVENTOR(S) : Shidong Yi et al.

Page 1 of 1

It is certified that error appears in the above-identified patent and that said Letters Patent is hereby corrected as shown below:

On the Title Page

Column 1, (73) Assignee name should be corrected as follows:
Sichuan Kelun Pharmaceutical Research Institute Co., Ltd.

In the Claims

Claim 4, Line 7, should be corrected as follows:
21.0±0.2°, 22.2±0.2°, 23.8±0.2°, 24.9±0.2°.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*